United States Patent [19]

Tricaud et al.

[11] Patent Number: 5,660,190
[45] Date of Patent: Aug. 26, 1997

[54] COSMETIC COMPOSITIONS FOR BLEACHING THE HAIR, PREPARATION, PROCESS AND USE THEREOF

[75] Inventors: Caroline Tricaud, Cormeilles en Parisis; Jean-Marie Millequant, Saint-Maur des Fosses; Henri Sebag, Paris, all of France

[73] Assignee: L'Oreal, Paris, France

[21] Appl. No.: 396,726

[22] Filed: Mar. 1, 1995

[30] Foreign Application Priority Data

Mar. 2, 1994 [FR] France ................... 94 02392

[51] Int. Cl.⁶ .............................. A61K 7/13; A61K 7/135
[52] U.S. Cl. .................... 132/208; 132/202; 132/203; 132/204; 132/205
[58] Field of Search ........................ 132/202, 203, 132/204, 205, 208, 209; 424/62, 47, 60, 70.9, 70.11, 63, 70.12, DIG. 3; 8/101, 107, 109, 110, 111

[56] References Cited

U.S. PATENT DOCUMENTS 4,027,008  5/1977  Sokol ........................ 424/62
4,327,751  5/1982  Evans .
4,994,088  2/1991  Ando et al. ................ 8/426
5,080,889  1/1992  Katada et al. ............. 424/63
5,468,477  11/1995  Kumar et al. ............. 424/78.17

FOREIGN PATENT DOCUMENTS 0 574 696  12/1993  European Pat. Off. .
2 276 809  1/1976  France .
3 434 468  3/1986  Germany .

*Primary Examiner*—Gene Mancene
*Assistant Examiner*—Pedro Philogene
*Attorney, Agent, or Firm*—Finnegan, Henderson, Farabow, Garrett & Dunner, L.L.P.

[57] ABSTRACT

The invention relates to novel pulverulent cosmetic compositions for bleaching hair, containing at least one oxidizing agent selected from peroxidized compounds, and at least one polymer selected from polyethylene glycol, polypropylene glycol, a derivative of polyethylene glycol, and a derivative of polypropylene glycol, where the polymer is present in an amount of 10 to 27% by weight, the polymer is anhydrous and, at room temperature, both liquid and water-soluble. The invention also relates to a process for the preparation of such compositions and to their use for bleaching hair.

14 Claims, No Drawings

COSMETIC COMPOSITIONS FOR BLEACHING THE HAIR, PREPARATION, PROCESS AND USE THEREOF

The present invention relates to cosmetic compositions for bleaching the hair having improved properties. More particularly, it relates to bleaching compositions preferably in the form of fine, anhydrous, fluid, homogeneous and non-dusty powders which disperse fully in aqueous hydrogen peroxide solution thereby generating, without notable heating, poultices of stable viscosity, which are easy to apply and which have improved cosmetic properties.

It is known to bleach the hair using pastes (or poultices) applied directly to the hair and obtained by mixing, at the time of use, a bleaching composition based on peroxidized compounds (oxidizing agents) with water, or most often with aqueous hydrogen peroxide solution. As is known, the bleaching composition comprises a peroxidized compound (essential component), generally a sodium, potassium or ammonium persulphate or perborate and sometimes a peroxycarboxylic acid salt or a peroxide, for example a peroxide of barium, of strontium, of urea or of melamine. Most often, these compositions also contain strongly alkaline agents such as alkali metal or alkaline-earth metal metasilicates, phosphates or carbonates (pH regulators). Finally, they may, moreover, optionally contain other additives or adjuvants common in this field: agents for controlling the release of oxygen during the mixing with aqueous hydrogen peroxide solution, such as magnesium carbonate or magnesia, thickening agents, such as cellulose derivatives (for example carboxymethyl cellulose) or starch and derivatives thereof, or alternatively guar gum, xanthan gum and alginates; surface-active agents, in particular anionic ones (especially alkyl sulphates); dyes; sequestering agents; fragrances. Such bleaching compositions are described, for example, in "The Science of Hair Care" by C. Zviak, Marcel Decker Inc. 1986, pp 225–226, the entire disclosure of which pages is hereby incorporated by reference.

The hair-bleaching compositions most widely used to date are provided in the form of powders (mixtures) of small particle size, i.e., with particles whose size is generally less than a millimeter, preferably less than a few hundred microns, thereby allowing easy and rapid dissolution and/or dispersion in aqueous hydrogen peroxide solution.

However, on account of the finely divided state in which they are found, such pulverulent compositions have several drawbacks: they are highly volatile and thus give off, during their handling, harmful dusts that contain peroxidized compounds and are highly irritating to the lungs; moreover, these powders are not only difficult to handle but are also difficult to measure out, presenting fluffing and flowability problems.

To attempt to remedy the above-mentioned problems, Patent Application EP-A-0,560,088 has described a totally dust-free (or fines-free) hair bleaching powder obtained by adding an oil or a liquid wax to the initial mixture of powders (solid peroxide+solid vehicle based on the alkali metal salts and the various adjuvants described above).

However, although effectively denser and less dusty than conventional bleaching powders, the bleaching powder described in EP-A-0,560,088 turns out to have other disadvantages, due in particular to the presence of oil or of wax, which may considerably limit the value of its use. Thus, with this powder, it is observed: that the mixtures with aqueous hydrogen peroxide solution take a long time to prepare and give shiny poultices of oily appearance; that removal of the product from the hair under forcing conditions is long and tedious; that the shampoos used to facilitate this removal after bleaching no longer form foams; and finally, that after the bleaching operation, the hair retains an unpleasant greasy and lank feel.

Moreover, Patent Application DE-A-3,434,468 has described a process for obtaining hydrogen peroxide addition compounds in the form of powders having, on the one hand, good flow properties and, on the other hand, good stability on storage, by dry-mixing of these compounds in powder form with from 0.5 to 5.0% by weight of a polyalkylene glycol having a molecular weight between 200 and 4,000 and comprising 2 to 3 carbon atoms in the alkyl group. Such powders may be used in particular for the preparation of bleaching powders.

However, with such polyalkylene glycol contents, the poultices obtained by mixing these powders with aqueous hydrogen peroxide solution become very hot, have a viscosity which is unstable over time, are too thick and are difficult to apply. In addition, the hair bleached using these poultices is coarse and difficult to disentangle, either when wet or dry.

Following considerable research into this matter, the inventors have found that it is possible to obtain hair-bleaching cosmetic compositions in powder form which can have none of the above-mentioned undesirable effects associated with the compositions of the prior art, by introducing a specific polymer into these cosmetic compositions in a proportion of approximately 10 to 27% by weight relative to the total weight of the composition. This discovery forms the basis of the present invention.

Thus, according to the present invention, novel pulverulent anhydrous cosmetic compositions for bleaching the hair are now proposed, comprising at least one oxidizing agent selected from peroxidized compounds and at least one polymer selected from polyethylene glycol, polypropylene glycol, a derivative of polyethylene glycol, and a derivative of polypropylene glycol. Preferably, the derivative of polypropylene glycol is a polyoxypropylene ether of butanediol of the formula:

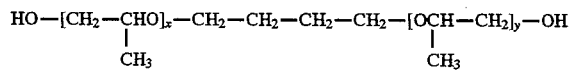

where x+y has an average value of 10. The polymer is present in an amount of 10 to 27% by weight relative to the entire composition, and the polymer is anhydrous and, at room temperature, both liquid and water-soluble.

The process for the preparation of the bleaching powders according to the invention, which itself constitutes a second subject of the present invention, comprises mixing, in the absence of a solvent and at room temperature, a conventional dry bleaching powder based on solid peroxidized compounds, with a polymer and in a proportion as defined above.

According to the invention, bleaching compositions provided in the form of fine but nonetheless dense and non-volatile powders (absence of fluffing) can thus be obtained. They can, in addition, be anhydrous and flow well (little lumping together, greater ease of measuring out). Moreover, their mixing with aqueous hydrogen peroxide solution can be rapid and simple, and preferably leads to poultices which do not heat up much and whose viscosity is stable over time; in addition, they are preferably very homogeneous, less thick and easier to apply; the bleached hair, wet or dry, disentangles better and is less coarse and grating. Moreover, these poultices are preferably smooth, creamy, lump-free and of much nicer appearance than those obtained with powders treated with mineral oils, such as silicone oils or paraffin oils, or waxes. In addition, these poultices are preferably easy to apply and adhere well to the hair without slipping. Finally, these poultices are preferably considerably easier to remove than is the case for powders containing oil or containing wax; the shampoos form foams, and the hair is not greasy, remains shiny and retains a natural feel.

However, other characteristics, aspects and advantages of the invention will emerge even more clearly on reading the description which will follow, as well as the various concrete, but in no way limiting, examples intended to illustrate it.

The polymers used in the context of the present invention are products that are already well known per se and that may readily be synthesized by those skilled in the art. Moreover, they are widely commercially available.

As indicated above, these polymers belong to the general family of polyethylene glycols (PEG) or of polypropylene glycols (PPG) or derivatives thereof, i.e., polymers whose main chain consists essentially of a repetition of units derived from ethylene oxide or from propylene oxide respectively. These polymers are prepared conventionally according to a polyaddition reaction, performed in a known manner, in the presence of a reaction initiator which may consist of any compound having a labile hydrogen atom (for example water, ethylene glycol, propylene glycol or any other alcohol or polyol). In this regard, polyethylene glycol derivative or polypropylene glycol derivative is understood here to more particularly denote, and to cover, polyaddition products which are obtained by using initiators other than those which are usually used for the preparation of a genuine polyethylene glycol or a genuine polypropylene glycol (i.e., water, ethylene glycol or propylene glycol). An example of such a polypropylene glycol derivative is PPG-10 butanediol, a compound which is commercially available from PPG Industries under the name MACOL 57. PPG-10 butanediol is a polyoxypropylene ether of butanediol and has the formula

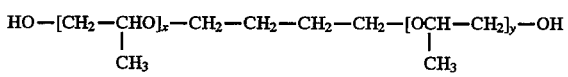

where x+y has an average value of 10. PPG-10 butanediol is a polyaddition product of 10 mols of polypropyleneoxide with 1 mol of butanediol. In this case, the initiator is the butanediol. According to an important characteristic of the present invention, among the above polymers only those are retained which are (i) anhydrous, (ii) liquid at room temperature and (iii) water-soluble at room temperature. Room temperature is understood here to denote a temperature which may be range from 15° C. to 30° C. approximately. Moreover, liquid is more particularly understood to denote a product whose viscosity is less than 1,000 centipoises, preferably less than 100 centipoises. Anhydrous is understood to mean that the water content of the product is less than 1% by weight, preferably less than 0.5% by weight. Finally, water-soluble is more particularly intended to mean a polymeric product whose water-solubility is at least 1 g/l and preferably at least 10 g/l.

According to the present invention, it is, of course, possible to use one or more of the polymers as are defined above.

The proportion of polymer(s) in the bleaching compositions according to the invention ranges from 10 to 27% by weight approximately relative to the total weight of the said composition. Preferably, this content ranges from 10 to 25% by weight approximately and, more preferably, from 10 to 20% by weight approximately.

The other essential (peroxidized compounds as oxidizing agents) or optional (pH regulators, thickening agents, cosmetic additives and the like) constituents entering (or which may enter) into the composition of the products according to the invention are those which are usually encountered for hair-bleaching compositions, in particular those indicated in the introductory part of the present description, which are entirely suitable here.

As a guide, the hair-bleaching formulations in accordance with the invention generally have the following compositions:

oxidizing agent(s) (preferably chosen from alkali metal persulphates): from 20 to 60% by weight, preferably from 30 to 50% by weight, relative to the entire formulation;

polymer(s): as indicated above;

pH regulator(s) (preferably chosen from alkali metal metasilicates): from 5 to 15% by weight, preferably from 9 to 14% by weight, relative to the entire formulation;

thickening agent(s): from 0.5 to 5% by weight, preferably from 1 to 3% by weight, relative to the entire composition;

optional cosmetic adjuvant(s): qs 100% by weight.

As indicated above, the bleaching compositions according to the invention are solids provided in a pulverulent powder form. The particles constituting this powder are generally smaller than 1,000 microns (1 mm) in size, but above all have a particle size distribution such that the weight content of the particles smaller than or equal to 65 microns in size (fines content) is remarkably low. Thus, this fines content is generally less than 1% by weight. This characteristic is such that the powders according to the invention are non-dusty. The maximum particle size indicated above itself makes the mixtures with aqueous hydrogen peroxide solution much easier to prepare.

According to a first embodiment of the process for the synthesis of the bleaching compositions according to the invention, conventional dry bleaching powders based on peroxidized compounds (i.e., powders which it is desired in particular to make non-volatile) are introduced into a mechanical mixer (mixer or LÖDIGE or WINKWORTH type in particular). These powders are then stirred, followed by incorporation into the latter of the polymer or polymers in accordance with the invention, and everything is mixed together, still with mechanical stirring, in order to achieve homogenization, and the resulting product which constitutes the composition according to the invention is finally recovered.

According to another embodiment, the liquid polymer or polymers in accordance with the invention is (are) pulverized simply (for example by spraying) onto the initial bleaching powders which are kept stirring (mechanical stirring or stirring via a fluidized bed for example), and the resulting product which constitutes the composition according to the invention is then recovered.

The above two embodiments are preferably carried out at room temperature and without the use of intermediary solvents, such as water or organic solvents (dry-mixing), even at the step of introduction of the polymer. The initial powder/polymer(s) proportions are chosen in the same way as indicated above for the desired final compositions. In both cases, the mixing times enable the final particle sizes to be controlled.

The pulverulent bleaching compositions in accordance with the invention may then be used on the hair in a conventional manner which is known per se in the field of hair bleaching. Thus, for example, the bleaching compositions are mixed in the form of powders with an aqueous hydrogen peroxide solution at a concentration of 6–12% approximately by volume, preferably at a concentration of 9% approximately by volume, and in a ratio generally of the order of 1:1, followed by mixing until a homogeneous paste is obtained, which is then applied to the hair and which is left in place for a period of between 25 and 45 minutes approximately. The composition is then removed from the hair (rinsing with water and/or shampooing).

Concrete examples illustrating the invention will now be given.

EXAMPLE 1

A bleaching composition in accordance with the invention (C1) which had the following composition (% by weight) was prepared:

| | | |
|---|---|---|
| Potassium persulphate | 40% | |
| Ammonium persulphate | 15% | |
| Sodium metasilicate | 12% | |
| Ammonium chloride | 5% | |
| Sequestering agent | 1% | |
| Silica | 7% | |
| Polymer 1[(1)] | 20% | |

[(1)]polyethylene glycol containing 80 mol of EO, of average molecular weight 400, sold under the brand name BREOX PEG 400 by the company BP.

The procedure was as follows: the various solid compounds constituting the initial bleaching powder (i.e., not containing the polymer) were introduced into a L ÖDIGE-type mixer, they were dry-mixed for 20 minutes in the mixer and the polymer acting as coating agent was then introduced into this mixer, and everything was mixed together (still dry) to achieve homogenization, for 20 minutes.

The particle size of the final bleaching powder obtained (determined by screening) is indicated in the table given below (C1). This table indicates the % by weight of the particles present in the composition, the size of which particles was within a given size range.

As a comparison, the particle size of the bleaching powder before introduction of the polymer (C0) is also indicated in this table.

When mixed weight for weight with 80 volumes of aqueous hydrogen peroxide solution, composition C1 only heated up by 6° C. over 10 minutes, whereas a similar mixture of a composition C'1 (which contained only 5% of polymer 1 instead of 20%, all factors remaining otherwise equal) heated up by 18° C.

In addition, when mixed weight for weight with 30 volumes aqueous hydrogen peroxide solution, composition C1 led to a poultice of initial viscosity equal to 174 cp and of viscosity equal to 194 cp after a dead time of 30 minutes. Under these conditions, the comparative composition C'1 led to a poultice whose initial viscosity of 2870 cp fell to 1880 cp.

Hair bleached with the composition C1 was soft and easy to disentangle. Hair bleached with the composition C'1 was coarser and harder to disentangle.

EXAMPLE 2

By repeating the procedure described in Example 1, a second composition in accordance with the invention (C2) similar to that of Example 1 was prepared, with the only two differences being that the polymer 1 was replaced here by a polypropylene glycol having an average molecular weight of 260, sold under the brand name PPG PM 260 by the company ALDRICH, and that the latter was used in an amount of 18% by weight.

The particle size of the final bleaching powder obtained (determined by screening) is indicated in the table given below (C2).

EXAMPLE 3

By repeating the procedure described in Example 1, a third composition in accordance with the invention (C3) similar to that of Example 1 was prepared, with the only two differences being that the polymer 1 was replaced here by a polypropylene glycol having an average molecular weight of 725, sold under the brand name PPG PM 725 by the company ALDRICH, and that the latter was used in an amount of 18% by weight.

The particle size of the final bleaching powder obtained (determined by screening) is indicated in the table given below (C3).

EXAMPLE 4

By repeating the procedure of Example 1, a fourth composition in accordance with the invention (C4) was prepared, this time having the following weight composition:

| | | |
|---|---|---|
| Potassium persulphate | 25% | |
| Ammonium persulphate | 25% | |
| Sodium metasilicate | 10% | |
| Ammonium chloride | 5% | |
| Sequestering agent | 2% | |
| Silica | 13% | |
| Polymer 4[(2)] | 20% | |

[(2)]PPG-10 Butanediol (CTFA) sold under the brand name MACOL 57 by the company PPG Industries.

The particle size of the final bleaching powder obtained (determined by screening) is indicated in the table given below (C4).

The particle size of the powder mixture before introduction of the polymer was identical to that of the composition C0 of Example 1.

TABLE 1

| Size $\Phi$ ($\mu$m) | C0 | C1 | C2 | C3 | C4 |
|---|---|---|---|---|---|
| $\Phi$ >710 | 2.2 | 47.50 | 31.04 | 27.70 | 32.00 |
| 355< $\Phi$ <710 | 7.8 | 19.34 | 22.48 | 30.94 | 50.60 |
| 100< $\Phi$ <355 | 28.46 | 17.94 | 20.74 | 17.92 | 13.11 |
| 60< $\Phi$ <100 | 52.86 | 13.72 | 25.40 | 13.00 | 3.26 |
| 0< $\Phi$ <60 | 7.74 | 0.40 | 0.24 | 0.16 | 0.00 |

The four compositions C1, C2, C3 and C4 lacked any dust.

What is claimed is:

1. A cosmetic composition for bleaching hair comprising at least one oxidizing agent selected from peroxidized compounds and at least one polymer selected from polyethylene glycol, polypropylene glycol, a derivative of polyethylene glycol, and a derivative of polypropylene glycol;

wherein said polymer is present in an amount of 10 to 27% by weight;

wherein said polymer is anhydrous and, at room temperature, both liquid and soluble in water; and wherein said composition is anhydrous and is in the form of particles of pulverulent powder.

2. A composition according to claim 1, wherein said derivative of polypropylene glycol is a polyoxypropylene ether of butanediol of the formula:

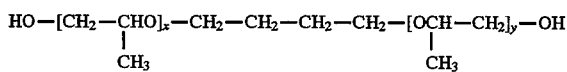

wherein x+y has an average value of 10.

3. A composition according to claim 1, wherein the content of polymer(s) ranges from 10 to 25% by weight.

4. A composition according to claim 3, wherein said content ranges from 10 to 20% by weight.

5. A composition according to claim 1, wherein the content of oxidizing agents of peroxidized-compound type ranges from 20 to 60% by weight.

6. A composition according to claim 5, wherein said content ranges from 30 to 50% by weight.

7. A composition according to claim 5, wherein the peroxidized compounds are chosen from alkali metal persulphates.

8. A composition according to claim 1, wherein less than 1% by weight of said particles are smaller than or equal to 65 microns in size.

9. A composition according to claim 1, wherein said particles are smaller than 1,000 microns (1 mm) in size.

10. A process for the preparation of a composition according to claim 1, the process comprising mixing, in the absence of a solvent and at room temperature, a dry bleaching powder based on solid peroxidized compounds, with a polymer and in a proportion as defined in claim 1, for a time sufficient to obtain said composition of claim 1.

11. A process for bleaching hair, comprising the step of contacting hair with the composition according to claim 1.

12. A process for bleaching hair, comprising the step of contacting hair with the composition obtained according to the process of claim 10.

13. A process for bleaching hair, comprising mixing a composition as defined in claim 1 with aqueous hydrogen peroxide solution; applying the resulting mixture to the hair; leaving the mixture in place; and removing the composition from the hair.

14. A process for bleaching hair, comprising mixing a composition obtained according to the process of claim 10 with aqueous hydrogen peroxide solution; applying the resulting mixture to the hair; leaving the mixture in place; and removing the composition from the hair.

* * * * *